US005206178A

United States Patent [19]

Monji et al.

[11] Patent Number: 5,206,178

[45] Date of Patent: Apr. 27, 1993

[54] MEMBRANE AFFINITY CONCENTRATION IMMUNOASSAY

[75] Inventors: Nobuo Monji; Carol-Ann Cole, both of Seattle, Wash.

[73] Assignee: Genetic Systems Corporation, Redmond, Wash.

[21] Appl. No.: 663,193

[22] Filed: Feb. 28, 1991

Related U.S. Application Data

[63] Continuation of Ser. No. 108,451, Oct. 20, 1987, abandoned, which is a continuation-in-part of Ser. No. 932,656, Nov. 19, 1986, abandoned.

[51] Int. Cl.[5] ...................... G01N 33/538; C12Q 1/00

[52] U.S. Cl. .................................... 436/518; 436/539; 436/810; 435/5; 435/7.1; 435/7.92; 435/7.93; 435/7.94; 435/7.95; 435/180; 435/971

[58] Field of Search ................... 435/5, 174, 180, 971, 435/974; 436/539, 541, 162, 174, 178, 810, 518

[56] References Cited

U.S. PATENT DOCUMENTS

| | | | |
|---|---|---|---|
| 4,407,943 | 10/1983 | Cole et al. | 436/528 |
| 4,434,150 | 2/1984 | Azad et al. | 436/530 |
| 4,451,568 | 5/1984 | Schneider et al. | 435/181 |
| 4,455,370 | 6/1984 | Bartlesman et al. | 435/6 |
| 4,486,530 | 12/1984 | David et al. | 436/529 |
| 4,504,585 | 3/1985 | Reynolds | 436/518 |
| 4,511,478 | 4/1985 | Nowinski et al. | 436/531 |
| 4,530,900 | 7/1985 | Marshall | 436/536 |
| 4,551,426 | 11/1985 | Freytag et al. | 436/512 |
| 4,609,707 | 9/1986 | Nowinski et al. | 436/535 |
| 4,649,105 | 3/1987 | Kasahara et al. | 436/518 |
| 4,666,866 | 5/1987 | Krauth | 436/518 |
| 4,703,017 | 10/1987 | Campbell et al. | 436/518 |
| 4,711,840 | 12/1987 | Nowinski et al. | 436/501 |
| 4,737,453 | 4/1988 | Primus | 435/5 |
| 4,742,011 | 5/1988 | Blake et al. | 436/518 |
| 4,767,701 | 8/1988 | Holmberg et al. | 436/531 |
| 4,780,409 | 10/1988 | Monji et al. | 435/7 |

FOREIGN PATENT DOCUMENTS

| | | |
|---|---|---|
| 0028132 | 5/1981 | European Pat. Off. . |
| 0040365 | 11/1981 | European Pat. Off. . |
| 0094777 | 11/1983 | European Pat. Off. . |
| 0125118 | 11/1984 | European Pat. Off. . |
| 2028091 | 3/1980 | United Kingdom . |

OTHER PUBLICATIONS

Oellerich, J. Clin. Chem, Clin. Biochem., vol. 22, 1984, pp. 895–904.

*Primary Examiner*—Christine M. Nucker
*Assistant Examiner*—Chris Dubrule
*Attorney, Agent, or Firm*—Townsend and Townsend

[57] ABSTRACT

Methods for determining the presence and/or concentration of an analyte in a biological fluid sample are disclosed. The methods generally include admixing in solution certain polymer/reactant and reporter/reactant conjugates along with the biological fluid sample suspected of containing the analyte, thereby forming ternary complexes. The separation of the complexes from the reaction mixture is achieved through the affinity of certain selected polymer compositions for various solid phases. Upon separation, the amount of reporter activity in the solution may be measured, and therefrom the presence and/or concentration of the analyte determined. Multiple analyses on a biological fluid sample suspected of containing one or more analytes may also be performed, using either a variety of different reporters or selected polymers having varied affinity for the solid phase.

34 Claims, 3 Drawing Sheets

$$* \ \frac{\text{BGG-FL/poly NIPAAM}}{\text{BGG-FL}}$$

MEMBRANE AFFINITY CONCENTRATION IMMUNOASSAY

This is a continuation of Ser. No. 07/108,451 now abandoned, which in turn is a continuation-in-part of Ser. No. 06/932,656, now abandoned.

TECHNICAL FIELD

The present invention relates generally to immunoassay methods, and more particularly, to a highly sensitive immunoassay in which a solid phase having an affinity for selected polymers is used to effect the separation of specifically bound reactants from free reactants.

BACKGROUND ART

Immunoassays

Immunoassays have found widespread application in the field of clinical diagnostics for the detection and measurement of drugs, vitamins, hormones, proteins, metabolites, microorganisms, and other substances of interest (analytes) in biological and non-biological fluids. Typically, these analytes occur in micromolar ($10^{-6}$M) or less concentration.

Immunoassays generally incorporate antibodies and antigens as reactants, at least one of which is labeled with a signal-producing compound (e.g., radioisotope, fluorophore, enzyme, etc.). Following mixture with the sample and incubation, specific antibody/antigen reactions occur (specific binding). The reaction mixture is subsequently analyzed to detect free and specifically bound labeled reactant, enabling a measurement of the analyte in the sample.

Immunoassays can be divided into two general categories, homogeneous and heterogeneous. In a homogeneous immunoassay, the signal emitted by the specifically bound labeled reactant is different from the signal emitted by the free labeled reactant. Hence, bound and free can be distinguished without physical separation.

The archetypal homogeneous immunoassay is the enzyme-multiplied immunoassay technique (EMIT) which is disclosed in U.S. Pat. No. 3,817,837. In this technology, analyte present in patient sample and analyte/enzyme conjugate compete for a limited amount of anti-analyte antibody. Specific binding of antibody to the conjugate modulates its enzymatic activity; hence, the amount of enzyme activity is proportional to the amount of analyte in the sample.

Homogeneous immunoassays have the advantages of being rapid, easy to perform, and readily amenable to automation. Their principal disadvantages are that they are relatively prone to interferences, are generally limited to low molecular weight analytes, and are generally limited in sensitivity to approximately $10^{-9}$M.

In a heterogeneous immunoassay, the signal emitted by the bound labeled reactant is indistinguishable from the signal emitted by the free labeled reactant; therefore, a separation step is required to distinguish between the two. Typical heterogeneous immunoassays include the radioimmunoassay (RIA) and the enzyme-linked immunosorbent assay (ELISA).

In the RIA, radiolabeled analyte and analyte present in patient sample compete for a limited amount of immobilized (solid-phase) anti-analyte antibody. The solid phase is washed to remove unbound, labeled analyte, and either the bound or the free fraction is analyzed for the presence of labeled reactant. ELISA assays are performed analogously. In the latter case though, the signal is an enzyme instead of a radioisotope. Heterogeneous immunoassays typically employ at least one reactant immobilized on a solid phase. Solids used to immobilize reactants in immunoassays have included controlled pore glass and preformed polymers, such as polyvinyls, polyacrylamides, polydextrans, and polystyrenes. Numerous separation methods are known in the art and have been used in heterogeneous immunoassays. These include centrifugation, micro-filtration, affinity chromatography, and gel-permeation chromatography. Since the kinetics of reaction between an immobilized antibody (or antigen) and its binding site tend to be slower than the kinetics of the same reaction occurring in solution, long incubation times are frequently required. When the multiple wash steps often needed are considered, it can be appreciated that heterogeneous assays tend to be time-consuming and labor-intensive. However, they are in general more sensitive than homogeneous assays and less prone to interferences, since interfering substances can be removed in the wash step(s).

Recently, a solid-phase immunoassay has been disclosed which is directed toward the concentration of signal to a very small surface area (EP 124,050; Jolley). Within this method, an analyte is reacted with an immunoreactant immobilized on water-insoluble particles (latex beads) in a substantially suspended state, and thereafter concentrated by microfiltration to a volume substantially less than the volume of the original sample. However, in addition to suffering from slow reaction kinetics, the use of latex beads as the solid phase contributes to high nonspecific binding. Further, since the signal bound to the latex beads collected on the filtration membrane is not physically bound to the membrane, this method is not suitable for a dipstick assay format, making it even less attractive for use in an efficient clinical setting.

Even more recently, an immunoassay has been developed in which membrane-linked antibody is used to immobilize an analyte, and immune reactions utilizing enzyme-linked antibody are carried out on a solid phase. Although this provides an improved method for concentrating signal within a small surface area, it still suffers from numerous disadvantages. These include slow reaction kinetics (because of the solid-liquid immune reaction), chemical modification of the membranes to covalently link the antibody to the membrane surface, high nonspecific binding of the membranes (generally nylon and glass fiber), a multiplicity of steps to carry out the assay, and the need for multiple high affinity antibodies. These disadvantages make this method practically unsuitable for detecting a wide variety of analytes within a clinical setting.

There is a need in the art, then, for an immunoassay which is highly sensitive, has fast-reaction kinetics, and which is readily amenable for use in efficiently detecting the presence of a variety of analytes within a clinical setting. The present invention fulfills this need and further provides other related advantages.

DISCLOSURE OF THE INVENTION

Briefly stated, the present invention discloses a method for determining the presence and/or concentration of an analyte in a biological fluid sample. The method generally comprises: (a) conjugating a first reactant which is capable of specifically binding with the analyte to a selected polymer to form a polymer/-reactant conjugate; (b) conjugating a second reactant which is capable of specifically binding with the analyte to a reporter to form a reporter/reactant conjugate; (c) admixing in solution the polymer/reactant, reporter/-reactant and the biological fluid sample suspected of containing the analyte to form a reaction mixture, such that specific binding occurs between the first and second reactants and the analyte, thereby forming a ternary complex; (d) contacting the reaction mixture with a solid phase capable of selectively binding the ternary complex, thereby removing the complex from the reaction mixture; and (e) measuring the amount of reporter activity in the bound complex or in solution and therefrom determining the presence and/or concentration of the analyte. The method may also include, after the step of contacting, washing the solid phase to remove nonspecifically bound reporter. In addition, the bound complex or only the reporter/reactant conjugate portion may be eluted from the solid phase. Alternatively, only the reporter portion of the bound complex may be eluted, as when the reporter is conjugated to the reactant by a labile linkage.

The polymer may be one characterized by a lower critical solution temperature. Particularly preferred polymers in this regard include N-alkylacrylamides, N-arylacrylamides, alkyl acrylates, aryl acrylates and combinations thereof. Further, the polymer may be a copolymer formed from selected monomers. In particular, the copolymer may be formed from N-isopropylacrylamide monomers and N-acryloxysuccinimide monomers copolymerized with a variety of monomers. Suitable acrylate monomers include n-amyl acrylate, isoamyl acrylate, n-octyl acrylate, methyl acrylate, ethyl acrylate, hexadecyl acrylate and 3,5,5-trimethylhexyl acrylate. Suitable acrylamide monomers include N-n-butylacrylamide, N-tert-butylacrylamide, N-decylacrylamide, N-tert-octylacrylamide, N-benzylacrylamide, N-iso-butoxymethylacrylamide, and diacetone acrylamide.

The first and second reactants are typically antibodies or antigens, although other reactants, such as lectins, receptors, transport proteins, peptides and non-immunoglobulin antibody-binding proteins may be used. Through the use of this method, the presence and/or concentration of a variety of analytes may be determined, such as drugs, vitamins, hormones, DNA, proteins, metabolites, cells, haptens, viruses, and micro-organisms. Reporters which may be used include enzymes, fluorophores, radio-isotopes, luminescers, and dye particles.

Another aspect of the invention discloses a method for determining the presence and/or concentration of an analyte in a biological fluid sample in which the reactant, such as an antibody or a drug, is conjugated to a monomer and copolymerized with additional monomers to yield a copolymer/reactant. Subsequent to conjugating a second reactant which is capable of specifically binding with the analyte to a reporter to form a reporter/reactant conjugate, the copolymer/reactant, reporter/reactant, and biological fluid sample suspected of containing the analyte are admixed in solution. Specific binding between the first and second reactants and the analyte is allowed to occur, thereby forming a ternary complex. The admixed copolymer/reactant, reporter/reactant, and analyte containing sample solution is then contacted with a solid phase capable of selectively binding the ternary complex, thereby removing the complex from the reaction mixture. The amount of reporter activity in the bound complex or in the solution may then be measured and therefrom the presence and/or concentration of the analyte determined. As noted above, the method may also include, after the step of contacting, washing the solid phase to remove nonspecifically bound reporter. In addition, the bound complex or only the reporter/reactant conjugate portion may be eluted from the solid phase. Alternatively, only the reporter portion of the bound complex may be eluted, as when the reporter is conjugated to the reactant by a labile linkage.

A third aspect of the present invention discloses a competitive assay format for determining the presence and/or concentration of an analyte in a biological fluid sample. The method generally comprises: (a) conjugating a reactant, such as a drug, to a selected polymer to form a polymer/reactant conjugate; (b) conjugating a reporter to a second reactant which is capable of specifically binding the analyte as well as the first reactant to form a reporter/reactant conjugate; (c) admixing in solution the polymer/reactant, reporter/reactant, and the biological fluid sample suspected of containing the analyte to form a reaction mixture; (d) incubating the mixture to allow competitive binding to occur between the analyte and the polymer/reactant for the second reactant; (e) contacting the polymer/reactant, reporter/reactant, and analyte containing mixture with a solid phase capable of selectively binding the polymer/-reactant-reporter/reactant complex and polymer/reactant, thereby removing the complexes and polymer/-reactant from the reaction mixture; and (f) measuring the reporter activity in the bound complex or in the solution and therefrom determining the presence and/or concentration of the analyte.

In an alternative format of a competitive assay for determining the presence and/or concentration of an analyte in a biological fluid sample, the method generally comprises: (a) conjugating a reactant, such as an antigen, to a selected polymer to form a polymer/reactant conjugate; (b) conjugating a reporter to a second reactant which is capable of competing with the analyte for binding to the first reactant to form a reporter/reactant conjugate; (c) admixing in solution the polymer/-reactant, reporter/reactant, and the biological fluid sample suspected of containing the analyte to form a reaction mixture; (d) incubating the mixture to allow competitive binding to occur between the analyte and the reporter/reactant for the polymer/reactant; (e) contacting the polymer/reactant, reporter/reactant, and analyte containing mixture with a first solid phase capable of selectively binding the polymer/reactant-analyte, polymer/reactant-reporter/reactant complexes, and polymer/reactant, thereby removing the complexes and polymer/reactant from the reaction mixture to form a resultant solution; (f) immobilizing on a second solid phase a third reactant which is capable of specifically binding the reporter in the reporter/reactant conjugate to form a reactant-activated solid phase; (g) contacting the resultant solution of step (e) with the reactant-activated solid phase, thereby removing the reporter/-reactant from the resultant solution; and (h) measuring the reporter activity in the bound reporter/reactant and therefrom determining the presence and/or concentration of the analyte.

A fourth aspect of the present invention discloses yet another method for determining the presence and/or concentration of an analyte in a biological fluid sample.

The method generally comprises: (a) contacting a polymer/reactant conjugate capable of specifically binding with the analyte with a solid phase capable of selectively binding with the polymer; (b) contacting the polymer/reactant-solid phase with a biological fluid sample suspected of containing the analyte such that specific binding occurs between the polymer/reactant (bound to the solid phase) and the analyte; (c) contacting the solid phase having polymer/reactant/analyte complexes bound thereto with a reporter/reactant conjugate capable of specifically binding with the analyte, such that specific binding occurs between the reporter/reactant and the analyte, the reporter being adapted to generate a signal that is quantitatively related to the presence and/or concentration of the analyte; and (d) measuring the amount of reporter activity in the bound complex and therefrom determining the presence and/or concentration of the analyte.

Yet another aspect of the present invention discloses a method for conducting multiple analyses on a single biological fluid sample suspected of containing one or more analytes. The method generally comprises: (a) conjugating a plurality of selected first reactants capable of specifically binding with one of the analytes to selected polymers to form multiple polymer/reactant conjugates; (b) conjugating a plurality of selected second reactants capable of specifically binding with one of the analytes to one or more reporters to form multiple reporter/reactant conjugates; (c) admixing in solution the multiple polymer/reactant, multiple reporter/reactant, and the biological fluid sample suspected of containing one or more analytes, such that specific binding occurs between the reactants and the analytes, thereby forming a plurality of ternary complexes; (d) contacting the admixed polymer/reactant, reporter/reactant, and analyte sample containing solution with a solid phase capable of selectively binding the ternary complexes, thereby removing the complexes from the reaction mixture; and (e) measuring the reporter activity in each of the bound complexes or in the solution and therefrom determining the presence and/or concentration of each of the analytes. As noted above, the method may also include, after the step of contacting, washing the solid phase to remove nonspecifically bound reporter. In addition, the bound complex or only the reporter/reactant conjugate portion may be eluted from the solid phase. Alternatively, only the reporter portion of the bound complex may be eluted, as when the reporter is conjugated to the reactant by a labile linkage.

An alternative mode for carrying out multiple analyte analyses includes conjugating a number of first reactants to a variety of polymers which have varied degrees of affinity for a solid phase. Each reactant in this regard is capable of binding to a specific analyte. A number of second reactants may be conjugated to the same or different reporters, and are capable of binding to each analyte of interest. The collection of polymer/reactants, reporter/reactants and the biological fluid sample suspected of containing the multiple analytes is then admixed in solution. Ternary complexes are allowed to form, and the solution subsequently contacted with a solid phase under conditions which allow the complexes to bind to the solid phase. Each different ternary complex is then eluted from the solid phase using conditions appropriate for the polymer complexed with the analyte of interest. Increasing concentrations of ionic detergents, non-ionic detergents, chaotropic agents, etc., can be used in a stepwise manner to sequentially remove the analyte containing complexes that are bound to different polymers. The eluent is measured for reporter activity, and therefrom the presence and/or concentration of the analyte determined.

Other aspects of the invention will become evident upon reference to the following detailed description and attached drawings.

BEST MODE FOR CARRYING OUT THE INVENTION

Figure 1:
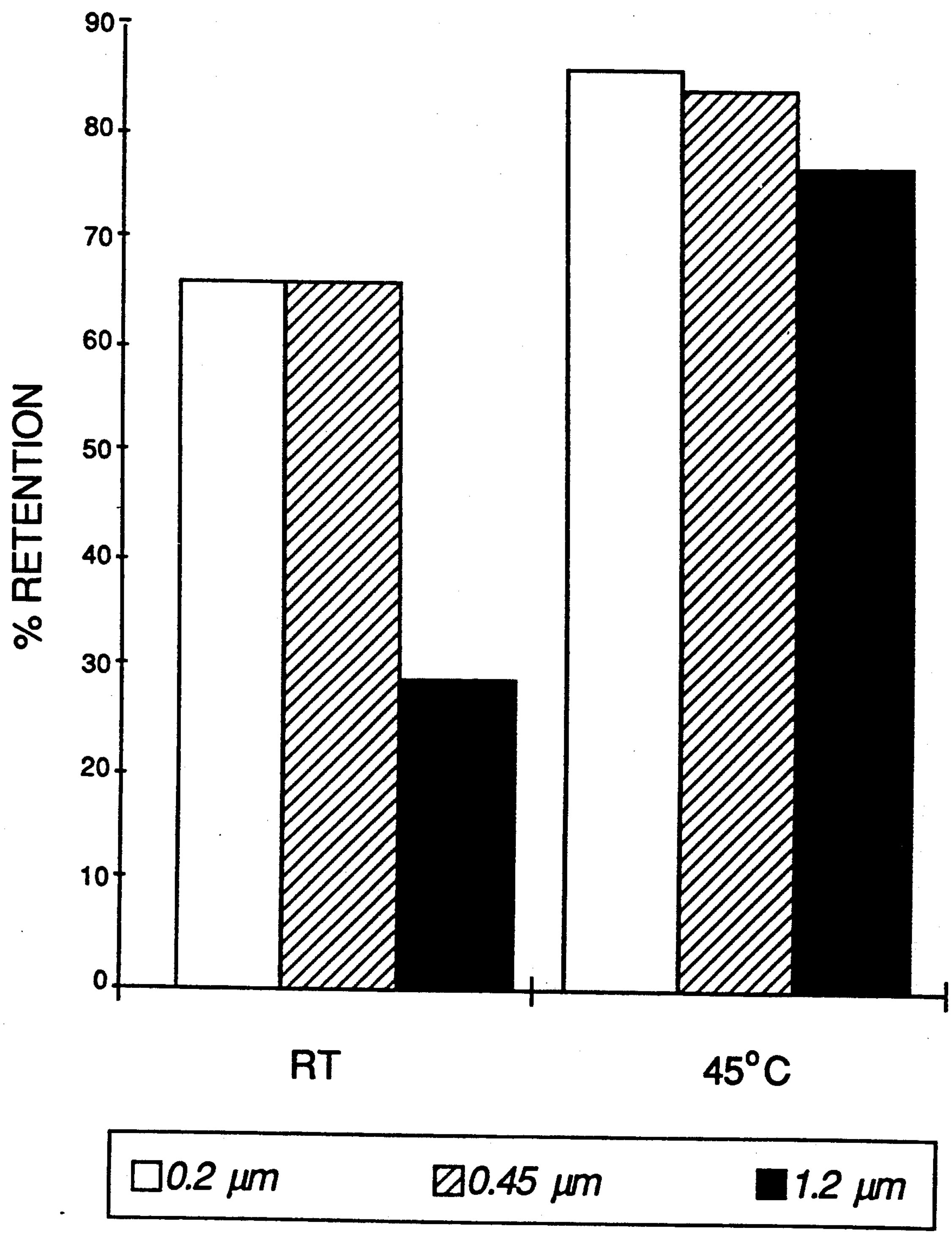
FIG. 1 depicts the retention of fluorescence on cellulose acetate membranes of different sizes at room temperature or at 45° C.

Prior to setting forth the invention, it may be helpful to an understanding thereof to set forth definitions of certain terms to be used hereinafter.

Analyte—is a substance or group of substances, the presence or amount of which it is desired to determine.

Biological fluids—are blood, blood serum, blood plasma, urine, feces, cerebrospinal fluid, saliva, sputum, cell- and tissue-derived extracts, etc., in which an analyte is suspected of being contained.

Reactants—are naturally occurring or synthetic substances, typically antigens and antibodies, which are capable of recognizing and specifically binding to an analyte of interest.

Antigen—as used herein includes molecules which themselves may induce antibodies as well as small molecules which are not capable of eliciting antibody production unless they are coupled to a carrier (e.g., haptens).

Specific binding reactions—are reactions characterized in that the reactants have an affinity for each other of at least $10^{-6}$M, more often at least $10^{-8}$M, and preferably at least $10^{-9}$M.

Reporter—is any substance which is capable of producing a detectable signal, either alone or in combination with other reagents, such as, for example, radioisotopes, fluorophores, chromophores, luminescers, and enzymes.

Selected polymer—a naturally occuring, synthetic, or semisynthetic molecule formed from smaller molecular units which is capable of selectively binding to a particular solid phase.

Although the following discussion pertains primarily to the immunoassay of analytes in biological fluids, it will be appreciated that there are numerous disciplines which require the assay of fluid samples for the presence or amount of organic substances. These disciplines include, for example, food preparation and environmental quality control.

In the present application, polymers are used in cooperation with selected solid phases to detect the presence and/or concentration of an analyte of interest. The separation of bound complexes from a reaction mixture is achieved by utilizing the affinity of certain polymer compositions for various solid phases. A variety of polymers may be useful within the present invention, depending in part upon their affinity for a particular solid phase. Suitable synthetic polymers may be formed from a single monomeric species (homopolymers) or preferably from a mixture of different monomers (copolymers). Representative classes of polymers useful within the present invention include those composed of N-alkylacrylamides, N-arylacrylamides, alkyl acrylates, aryl acrylates and combinations thereof.

Temperature-Sensitive Polymers

In a particularly preferred embodiment of the present invention, conjugates of reactants with polymers exhibiting a lower critical solution temperature (polymer/reactant conjugates) are utilized.

Certain water-soluble polymers are known to precipitate when a critical solution temperature is reached (Molyneux, *Water Soluble Synthetic Polymers: Properties and Behavior*, CRC Press, Boca Raton, Fla., 1983). The majority of polymers exhibit de-mixing behavior (phase separation) upon cooling. Such behavior is called "$\theta_-$ behavior" and the temperature at which de-mixing occurs is referred to as the upper critical solution temperature (UCST). However, certain polymers exhibit de-mixing behavior (phase separation) upon heating. Such behavior is called "$\theta_+$ behavior" and the temperature at which de-mixing occurs is referred to as the lower critical solution temperature (LCST).

Among polymers which exhibit a lower critical solution temperature are the following: polyvinyl methylether (PVME), polyvinylmethyl oxazolidone (PVMO), polymethacrylic acid (PMAA), poly-N-isopropyl acrylamide (PNIPAAm), hydroxypropyl cellulose (HPC), and methyl cellulose (MC). [Franks, in C. A. Finch, ed., *Chemistry and Technology of Water-Soluble Polymers*, New York, Plenum Press, 1983, p. 157] Any polymer or copolymer or monomers thereof, be they naturally occurring, synthetic, or semi-synthetic, which is capable of selectively binding to a particular solid phase following conjugation to a reactant can be used in the immunoassays of the present invention.

Particularly preferred are polymers or monomers of N-isopropylacrylamide and derivatives thereof. In addition, several monomers may be copolymerized with N-isopropylacrylamide monomers in order to produce particularly desirable copolymers. For instance, such monomers include N-n-butylacrylamide monomers and N-acryloxysuccinimide monomers. Two particularly preferred copolymers are N-isopropylacrylamide: N-acryloxysuccinimide, 100:2.5 (A-poly 5), and N-isopropylacrylamide: N-acryloxysuccinimide: N-n-butylacrylamide, 60:2.5:40 (A-poly 32). Suitable acrylate monomers include n-amyl acrylate, iso-amyl acrylate, n-octyl acrylate, methyl acrylate, ethyl acrylate, hexadecyl acrylate and 3,5,5-trimethylhexyl acrylate. Other suitable acrylamide monomers include N-tert-butylacrylamide, N-decylacrylamide, N-tert-octylacrylamide, N-benzylacrylamide, N-iso-butoxymethylacylamide, and diacetone acrylamide.

Polymer/Reactant Conjugates

Typically, the reactant is an antibody or an antigen; however, other reactants are known in the art, including, for example, lectins, receptors, transport proteins, and non-immunoglobulin antibody-binding proteins such as staphylococcal protein A. Where the reactant is an antibody, either monoclonal or polyclonal antibodies can be used. Prior to conjugation, the antibody will in general be at least partially purified by methods well known in the art.

The polymer can be preformed (pre-polymerized) and the reactant conjugated to the preformed polymer by conventional chemistry. For example, an activated ester of the reactant can be conjugated to reactive groups on the polymer. Alternatively, the reactant can be conjugated to a monomer and then copolymerized with additional monomers to yield a copolymer/reactant.

Purification of the polymer/reactant conjugate can be accomplished by any of a variety of methods well known in the art. For example, the conjugate can be purified by gel-permeation chromatography. Alternatively, it can be purified by serial precipitation of the polymer/reactant conjugate. If the latter method is used, care must be taken to ensure that the reactant is not denatured.

Gel-permeation chromatography and serial precipitation will suffice to remove free antibody from antibody-conjugated polymer but will not remove free polymer from the mixture. Separation of free polymer from antibody-conjugated polymer can be accomplished by chromatography on hydroxylapatite (HAP). The free polymer will pass through the column at conditions under which the antibody-conjugated polymer will bind to the column. The conjugate can subsequently be eluted by changing the ionic strength of the buffer in which chromatography is performed.

Reporter/Reactant Conjugate

In addition to a polymer/reactant conjugate, a reporter/reactant conjugate is required. The reactant can be selected from any of those described previously for the first reactant/polymer conjugate. Selection of the reactant is dependent on the assay mode, but should be reactive with a binding site on the analyte which can be the same or different than that site with which the first reactant is reactive. The reporter can be chosen from any of those known in the art, including enzymes, fluorophores, radioisotopes, luminescers, dye particles, etc. Some suitable fluorophores include fluorescein, rhodamine, phycoerythrin, phycocyanin, and nile blue. Among preferred enzymes are horseradish peroxidase (HRP), β-galactosidase (β-GAL), glucose oxidase, urease, β-lactamase, and alkaline phosphatase (AP). When the reporter is an enzyme, the step of measuring may include exposing the bound complex to substrate and incubating for color or fluorescence development. It will be evident to one skilled in the art that the particular substrate utilized will be dependent upon the enzyme chosen.

Solid Phases

Separation of free from specifically bound reporter/reactant conjugate is effected by contacting the ternary complex formed which consists of polymer/reactant, analyte and reporter/reactant with a solid phase capable of selectively binding the complex. Any free reporter/reactant conjugate that attaches nonselectively to the solid phase may be removed by washing the solid phase.

A variety of solid phases may be utilized within the methods described herein, including cellulose acetate and esters of cellulose, depending upon the particular polymers selected.

A particularly preferred solid phase for use herein is a cellulose acetate membrane. One advantage of this particular membrane is that it has very low nonspecific protein binding properties, which can be further minimized by treatment with bovine serum albumin (BSA). In addition, it has been determined that there is minimal interference by proteins and mild detergents to the binding of the complex to this membrane. When cellulose acetate is chosen as the solid phase, preferred polymers include poly-N-isopropylacrylamide or its derivatives. It is preferable when performing the immunoassay using this particular combination of polymer and solid phase to maintain a temperature above the LCST of the polymer.

In general, it is preferred that the antigen/antibody (or other specific binding) reaction take place at temperatures between about 0° C. and 55° C., more often between 22° C. and 45° C. In many instances, specific binding reactions can be enhanced by raising the temperature to between 37° C. and 45° C.

Although it is preferable to utilize poly-N-isopropylacrylamide or its derivatives in combination with cellulose acetate, it will be evident that a variety of other polymers may be suitable for use with this membrane. Generally, any polymer which is capable of selectively binding to the cellulose acetate membrane may be utilized. The affinity of a particular polymer for cellulose acetate or another solid phase may be readily determined, for example, through use of a relatively simple screening procedure. The polymer may be tested alone or conjugated to a reactant. Polymer, labeled with a radioactive tag or unlabeled, is admixed with the solid phase. If unlabeled, the flow through the solid phase is monitored for UV absorbance at 214 nm and the quantity of polymer adsorbed determined. If radioactively tagged, e.g., $^{125}I$, the solid phase is counted in a gamma counter, and again the quantity of polymer adsorbed is determined. The polymer, copolymer, or conjugates thereof should have an affinity of at least $10^{-2}$M; more commonly, at least $10^{-6}$M; and even more preferred, $10^{-10}$M, under the actual assay condition.

The step of contacting the solid phase with the reaction mixture containing the ternary complex may be accomplished in a variety of ways. Particularly preferred methods include filtering the reaction mixture through the solid phase or dipping the solid phase into the reaction mixture.

Alternatively, a polymer/reactant conjugate may be first contacted with a solid phase capable of selectively binding with the polymer, such that the polymer is bound to the solid phase. The solid phase having polymer bound thereto is then contacted with a biological fluid sample suspected of containing an analyte of interest. Subsequently, the solid phase having polymer/reactant/analyte complexes bound thereto is contacted with a reporter/reactant conjugate capable of specifically binding with the analyte, such that specific binding occurs. The reporter is adapted to generate a signal that is quantitatively related to the presence and/or concentration of the analyte, allowing one to measure the amount of reporter activity in the bound complex and therefrom determine the presence and/or concentration of the analyte.

Assay Modes

The immunoassays of the present invention can be performed in any of several configurations. These can include competitive, sandwich, and non-competitive immunoassay configurations. In every case, the analyte of interest can be an antigen or an antibody. In every case, the reactant (i.e., antigen or antibody) can be conjugated to either the polymer or to the reporter. The various possible configurations in which immunoassays can be performed are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); *Enzyme-Mediated Immunoassay*, T. T. Ngo and H. M. Henhoff, Plenum Press, New York (1985), and in numerous other publications.

Multiple analyses can be performed on a sample by choosing a variety of reporters, each reporter having a different specific binding partner conjugated thereto. The ternary complexes bound to a solid phase would then be analyzed for the presence of each reporter. Particularly preferred reporters in this regard include fluorescein and rhodamine. Alternatively, multiple analyses can be performed on a sample by choosing a variety of polymers which have varied degrees of affinity for a solid phase. Each polymer would have a different specific binding partner conjugated thereto, and the various ternary complexes would be selectively eluted from the solid phase under conditions appropriate for the particular polymer bound to an analyte of interest. The polymers may be eluted from the solid phase using a variety of substances, including ionic detergents, nonionic detergents, and chaotropic agents.

As noted above, there are a variety of alternatives to measuring the amount of reporter activity in the complex bound to the solid phase or free reporter in solution. In one such alternative, the entire bound complex is eluted from the solid phase, wherein agents for disrupting either hydrophobic interactions or hydrogen bonding, such as 0.2% sodium dodecyl sulfate or 4M potassium thiocyanate, can be used, while in another alternative only the reporter/reactant conjugate portion is eluted from the solid phase. It will be evident to one skilled in the art that the conditions required to release the reporter/reactant portion are dependent upon the reactant chosen. In yet another embodiment, only the reporter portion of the bound complex is eluted, as when the reporter is conjugated to the reactant by a labile linkage. By way of example, the reporter-reactant linkage might be a disulfide bond or a vicinal diol, and the linkage subsequently cleaved by the addition of a reducing or oxidizing agent, such as 2-mercaptoethanol or periodate, respectively, thereby releasing only the reporter portion of the bound complex.

Solid phase affinity concentration immunoassays offer many advantages over prior art immunoassays. First, specific binding reactions occur in solution rather than on a solid phase, hence the reaction kinetics are more favorable, leading to reduced incubation times.

Second, nonspecific binding is much lower than in conventional solid phase immunoassays, such as that taught by Jolley. This is due to the fact that conventional solid phases are hydrophobic and will adsorb proteins onto their surfaces. Further, in some prior art immunoassays, an additional solid phase is present throughout the assay, maximizing the opportunity for nonspecific binding to occur.

Third, a significant concentration effect is obtained, resulting in a highly sensitive immunoassay.

Fourth, the present invention is amenable to a dipstick assay format, since the specific signal bound to the membrane is an affinity phenomenon and is not easily removed. In addition, no prior modification or treatment of the membrane is necessary in order to achieve this result.

The following examples are offered by way of illustration and not by way of limitation.

EXAMPLE I

Synthesis and Characterization of Antibody-Conjugated A-poly 32

A. Preparation of A-poly 32: N-isopropylacrylamide, N-n-butylacrylamide, N-acryloxysuccinimide (60:40:2.5)

The conditions for copolymerization were analogous to those described by Pollack et al. (*J. Am. Chem. Soc.* 102: 6324-6336, 1980). A 100-ml two-necked, round-bottomed flask, fitted with a reflux condenser, thermometer, and nitrogen inlet controlled by a Firestone valve, was charged with N-isopropylacrylamide (2.99 g, 26.4 mM, Kodak #10982), N-n-butylacrylamide (2.24 g, 17.6 mM, Monomer-Polymer and Dajac Laboratories, Inc. #7872), N-acryloxysuccinimide (0.186 g, 1.1 mM, prepared by the method of Pollack et al., *J. Am. Chem. Soc.* 102: 6324-6336, 1980), azobis (isobutyronitrile) (0.021 g, 0.13 mM, Polysciences #0117), and THF (50 ml, pretreated to control peroxide contamination-deperoxidation by the procedure of D. R. Burfield, *J. Org. Chem. Soc.* 47: 3821-3824, 1982). The mixture was stirred, degassed, heated to 50°-55° C. internal temperature, maintained under positive nitrogen pressure for 24 hours, and allowed to cool to room temperature. The reaction mixture was filtered through a layer of glass wool as the filtrate was stirred into ethyl ether (200 ml). The precipitated product (A-poly 32) was collected by filtration, washed thoroughly with ethyl ether, and dried (40°-45° C.) under vacuum to yield 3.9 g.

B. Preparation of Activated Copolymer/McAb 2Hl Conjugate

Conjugation of monoclonal antibody 2Hl, an anti-human kappa light chain antibody (Genetic Systems Corporation, Seattle, Wa.) to the activated copolymer A-poly 32 was carried out as follows. Activated A-poly 32 (20 ug) was dissolved in 100 ul of dimethylformamide (DMF) and placed in ice. In a separate tube, 120 ul of mono-clonal antibody 2Hl (1.5 mg) was added to 2 ml of 0.1M Hepes buffer, pH 7.5, and placed on ice. The DMF solution containing the polymer was added to the antibody solution, and the tube was rinsed with 25 of DMF. The rinse was added to the antibody solution, and the mixture was kept on ice with intermittent vortex mixing until a homogeneous solution was formed. Once the solution was homogeneous, it was allowed to incubate in the refrigerator for the desired time, usually one to two days. At the conclusion of the incubation, the mixture was diluted with 4 ml of distilled water and allowed to come to room temperature before the addition of 2 ml of room-temperature, saturated ammonium sulfate solution. The resulting solution was centrifuged at room temperature (approximately 20° C., 1500 xg) for 15-20 minutes. The supernatant was removed and after 6 ml of distilled water were added, the solution was placed on ice to dissolve the precipitate. The mixture was allowed to come back to room temperature. The ammonium sulfate precipitation and centrifugation steps were repeated three more times. To the final precipitate 6 ml of distilled water was added and the solution was placed on ice to dissolve.

A hydroxylapatite column (1×1 cm) was equilibrated with distilled water at 4° C. and the redissolved precipitate was loaded onto it. The column was washed with distilled water until the optical density at 214 nm came back to baseline, signifying that the unconjugated copolymer had been washed from the column. The column temperature was raised to room temperature and the copolymer/monoclonal antibody conjugate was eluted with 0.3M phosphate buffer, pH 6.8. The collected fractions were monitored with a protein assay reagent and the fractions containing protein were pooled.

EXAMPLE II

Retention of Fluorescence on Cellulose Acetate Membrane

A. Studies With Membranes of Different Sizes at Room Temperature or at 45° C.

Fluoresceinated bovine gamma globulin (BGG-FL)/polyNIPAAm conjugate was dissolved in 1.0 ml of PBS containing 1% bovine seruma albumin (PBS/BSA). The solution was filtered through either 0.2, 0.45 or 1.2 um pore size cellulose acetate membrane (Schleicher and Schuell) either at room temperature or at 45° C., and the filtrate was saved. One half ml of the filtrate was added to 1.0 ml PBS and fluorescence was measured at $E_x$=495 nm and $E_m$=520 nm. Percentage retention of fluorescence (FL) as shown in FIG. 1 was calculated using the following equation:

$$\% \text{ retention of } FL = \frac{\text{Added } FL - FL \text{ in filtrate}}{\text{Added } FL}$$

All of the fluorescence values were corrected for the background fluorescence due to BSA.

Figure 2:
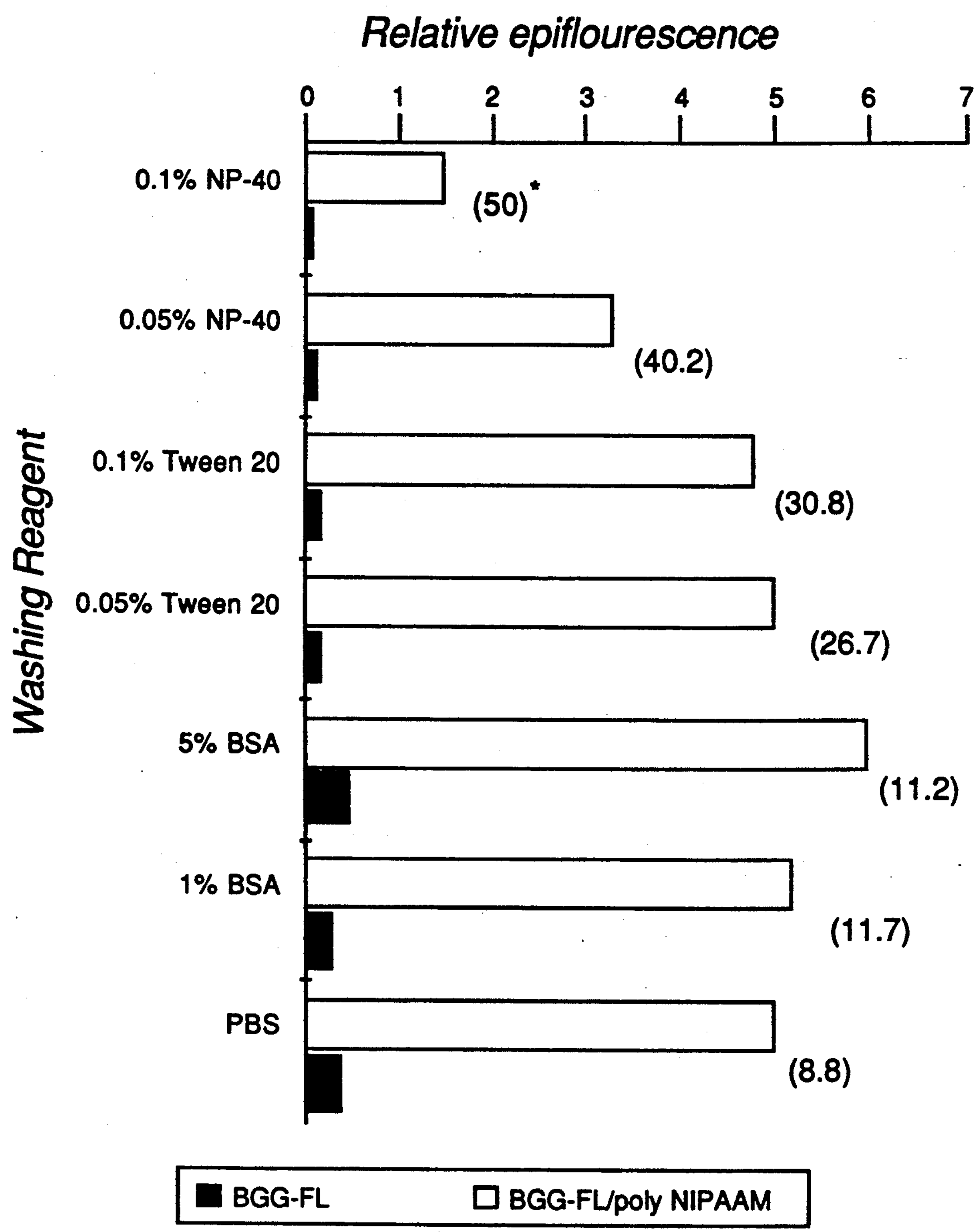
FIG. 2 depicts the retention of either BGG-FL/polyNIPAAm conjugates or BGG-FL on cellulose acetate membranes (0.2 um, Pandex plate) after removal of nonspecific binding by various proteins and detergents.

B. Retention of Either BGG-FL/polyNIPAAm Conjugate or BGG-FL After Removal of Nonspecific Binding by Washing BGG-FL/polyNIPAAm conjugate or BGG-FL was added to 0.5 ml of PBS/BSA. The solution was warmed to 45° C. and an aliquot (50 ul) added to the well which had been pretreated with PBS/BSA to minimize the nonspecific binding and which had been warmed to 45° C. The added solution was filtered at 45° C. by vacuum suction. Each well was washed by filtration two times with PBS/BSA (45° C.) and two more times with washing reagents (45° C.). After the last wash, each well was read for epifluorescence and the results are shown in FIG. 2.

Figure 3:
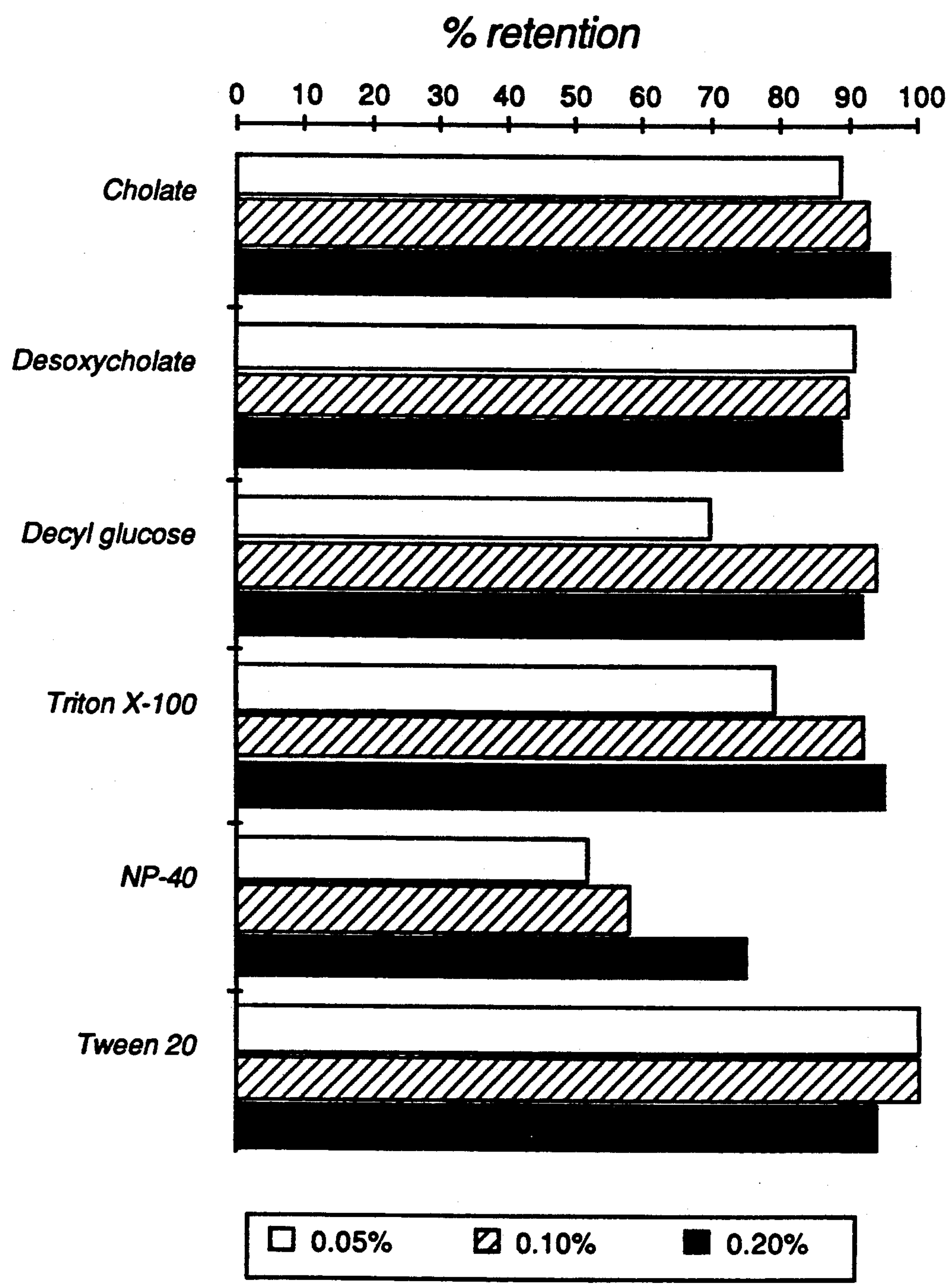
FIG. 3 depicts the retention of fluorescence on cellulose acetate membrane after the filtration of BGG-FL/polyNIPAAm solutions containing various detergents.

C. Retention After Filtration of BGG-FL/polyNIPAAm Solutions Containing Various Detergents BGG-FL/polyNIPAAm conjugate was added to a solution containing various detergents (final concentration of either 0.05, 0.1 or 0.2%, total volume of 0.5 ml). The solution was warmed to 45° C. and an aliquot (50 ul) was added to a well which had been warmed to 45° C. The added solution was filtered by vacuum suction and the well was washed by filtration two times with PBS/BSA (45° C.) and two more times with PBS (45° C.). After the last wash, each well was read for epifluorescence and the results are shown in FIG. 3.

EXAMPLE III

Retention of Ig/polymer Conjugates

A. Labeling of Ig/polymer Conjugate with Bolton-Hunter Reagent

Mouse IgG and IgM/polymer conjugates were labeled with N-succinimydyl 3-(4-hydroxy, 3-[$^{125}$I] Iodophenyl propionate ([$^{125}$I]-BHR) by dissolving 50 μCi of [$^{125}$I]-BHR in 50 μl of dimethylformamide (DMF) and adding the resulting solution to 0.5 ml HEPES buffer, pH 7.5, containing 100 μg of either murine IgG or IgM and incubating at room temperature for one hour. The reaction mixture was applied to a Sephadex G-25 gel filtration column equilibrated with HEPES buffer, pH 7.5 to separate the unconjugated [$^{125}$I]-BHR. The eluate containing both [$^{125}$I] reactivity and protein (~90 μg/2 ml), as determined by Coomassie Blue protein reagent, were pooled together and cooled to 4° before 100 μl of A-poly 32 in DMF (200 mg/ml) was added. The conjugation reaction was incubated 16–18 hours at 4° C. before purification of the [$^{125}$I]-Ig/A-poly 32 conjugate by $(NH_4)_2SO_4$ precipitation and hydroxylapatite chromatography, as described previously.

B. Retention of [$^{125}$I]-Ig/A-Poly 32 Conjugate on Cellulose Acetate Membrane Retention of immunoglobulin/A-poly 32 conjugate by A-poly 32 was tested by contacting the conjugate with the membrane and washing the membrane with a number of detergent washes and determining the amount of conjugate retained on the membrane. [$^{125}$I]-Ig/A-poly 32 (8000 cpm, about 0.1 μg) was dissolved in 200 μl of 1% BSA/Tris-saline and added to a well of a dot blot apparatus containing a sheet of pretreated (immersed in 1% BSA/PBS, 1 hr.) 1.2μ pore size cellulose acetate membrane. Filtration was accomplished by using an absorbent pad to pull the mixture through the membrane. The membrane was washed five times with 200 μl of 0.05% Tween 20 in Tris-buffered saline at 25° C. The filtration spot was cut out, and retained [$^{125}$I]-Ig/A-poly 32 conjugate was determined by counting gamma radioactivity. As shown in Table I, Ig/A-Poly 32 retained on cellulose acetate membrane was resistant to at least 5 washings with a detergent, Tween 20, after unbound material was washed away.

TABLE I

Ig/A-Poly 32 Retention by Cellulose Acetate Membrane Upon Washing

| Wash | CPM[$^{125}$I] on Membrane |
|---|---|
| 0 | 6722 |
| 1 | 4895 |
| 2 | 4677 |
| 3 | 4777 |
| 4 | 4467 |
| 5 | 4626 |

C. Effect of Cellulose Acetate Membrane Pore Size on Retention

Labeled Ig A-poly 32 was prepared as in Example III B above and retention was assayed in the same way. Cellulose acetate membrane of various pore sizes (0.2, 0.45, 0.8 and 1.2 μm) were used as the solid phase. Each well was washed twice with Tween 20 and the spot was cut and the amount of [$^{125}$I] Ig/A-poly 32 retained was determined. The results summarized in Table II demonstrate that the amount of Ig/A-poly 32 retained by a cellulose acetate membrane is independent of the pore size of the membrane and not due to physical entrapment of the conjugate.

TABLE II

Ig/A-Poly 32 Retention by Cellulose Acetate Membrane of Various Pore Sizes

| Membrane Pore Size (μm) | CPM[$^{125}$] Ig/A-Poly 32 |
|---|---|
| 0.2 | 16,413 |
| 0.45 | 17,003 |
| 0.8 | 15,719 |
| 1.2 | 16,293 |

D. Retention of [$^{125}$I]-Ig/A-Poly 32 by Various Membranes

Various other types of membranes were tested for their ability to retain [$^{125}$I]-Ig/A-poly 32 under the wash conditions used previously. Membrane substrates tested included polycarbonate, mixed ester, regenerated cellulose, nylon, and cellulose acetate. The procedure was as described in Example III. C. and each membrane was washed twice with 0.5% Tween 20/Tris-saline.

The % retention of radioactivity as shown in Table III was calculated using the following equation:

$$\% \text{ Retention of radioactivity} = \frac{\text{Radioactivity on membrane} - \text{Background (Radioactivity)}}{\text{Radioactivity on } CA \text{ membrane} - \text{Background}}$$

The results indicate that cellulose acetate is the best membrane substrate for retention of the reactant-/polymer conjugate although nylon does bind a small amount of polymer/reactant conjugate.

TABLE III

Ig/A-poly 32 Retention by Various Membrane Types

| Membrane | Pore Size (u) | Radioactivity (CPM) [$^{125}$I]-IgG/ A-Poly 32[1] | [$^{125}$I]-IgM/ A-Poly 32[2] |
|---|---|---|---|
| Poly-carbonate | 0.8 | 849 (0.8)[3] | 610 (0.2) |
| Mixed Ester | 0.8 | 771 (0.7) | 634 (0.2) |
| Regenerated Cellulose | 1.0 | 1,328 (1.7) | 2,169 (1.5) |
| Nylon | 1.2 | 7,327 (12.9) | 6,165 (4.8) |
| Cellulose Acetate | 1.2 | 54,006 (100) | 120,439 (100) |

[1]Total radioactivity [$^{125}$I]-IgG/A-Poly 32 used approximately 67,000 CPM
[2]Total radioactivity [$^{125}$I]-IgM/A-Poly 32 used approximately 150,000 CPM
[3]% Relative radioactivity

EXAMPLE IV

Antigen Capture Membrane Affinity Concentration Immunoassay for Human IgM

The assay was performed by adding the following reagents: 100 ul of A-poly5/MAb (2H1, 4.5 ug/assay) or A-poly 32/MAb (2Hl, 4.5 ug/assay) conjugate, fluoresceinated MAb reactive with the human mu chain 2C3, (Genetic Systems Corporation, Seattle, WA, 1.2 ug/assay), and 100 ul of human IgM standard in 1% BSA in PBS. The reaction mixture was incubated for 1 hour at room temperature, and then for 15 minutes at 45° C. or at 25° C. (room temperature). A 90 ul aliquot of the reaction mixture was transferred to a Pandex assay plate well which had been warmed to 45° C. The assay plate contained a 0.2 um cellulose acetate membrane which had been blocked with 100 ul of 0.1%

BSA/PBS for 1 hour. Filtration of the reaction mixture was carried out at 45° C. by vacuum suction, and another 90 ul of the reaction mixture was added to the same well and again vacuum suction filtered. The wells were washed twice by filtration with 1% BSA/PBS (100 ul) and two more times with 120 ul of PBS. After the final filtration, the fluorescence of each well was determined using a Pandex Screen Machine (Pandex Laboratories, Mundelein, Ill.), using the excitation wavelength (490 nm) and an emission wavelength of 520 nm. Both polymer conjugates 2HI/A-poly 5 and 2HI/A-poly 32 were able to detect Human IgM down to about 0.1 μg/ml. 2HI/A-poly 32 gave approximately the same values whether the assay was conducted at 25° or 45° C. while 2HI/A-poly 5 was more sensitive when run at 45° C.

EXAMPLE V

Detection of Rabbit Anti-Human IgG by a Second Antibody Sandwich Assay

A. Dipstick Format

A dipstick assay was formulated for Human IgG using as the solid phase cellulose acetate to which Ig/A poly 32 conjugate was stably immobilized. Human IgG (HIgG, Cappel Laboratories) was conjugated to A-poly 32 by the method of Example I.B. The final product was dissolved in PBS/1% BSA (40 μg/ml) and 50 μl (2 μg of antibody) was immobilized as a small circular dot (0.4 cm diameter) onto the cellulose acetate membrane using a Blot-Block filtration device. The membrane was dried at 25° C. overnight before a square piece (0.8 cm square) containing the H IgG/A-poly 32 spot was cut and mounted onto one end of a plastic strip (0.8 cm×9 cm) using Sprament (3M Company) a water resistant adhesive to form a dipstick. The dipstick was soaked for 10 minutes in 1% BSA/Tris-saline, air dried and stored at 4° C. Rabbit test serum suspected of containing anti-H IgG was serially diluted in 1 ml of sample diluent (2.5% [w/v] nonfat dry milk, 0.01% thimerosal, 0.005% Antifoam A in 20 mM sodium citrate). A dipstick was submerged in the test solution and incubated for 10 minutes. After incubation, the dipstick was thoroughly washed with Tris-saline and the excess was blotted out before submerging it into a solution of 1 ml sample diluent containing goat anti-rabbit Ig/alkaline phosphatase conjugate (Cappel Laboratories). The incubation was for 10 minutes and the dipstick was again thoroughly washed with Tris-saline, and blotted before the addition of substrate solution (1.25 mg 3-indoxl phosphate/ml 1M 2-amino 2-methyl-1 propanol, pH 10.3) for two minutes. The dipstick was again rinsed with Tris Saline to remove the excess substrate. Signal generation was observed visually or quantitated by reflectometry. Human Immunoglobulin G in serum from a rabbit hyperimmunized with human IgG was detectable at serum dilutions up to 1/500.

B. Filtration Format

Human IgG/A-poly 32 conjugate was immobilized as described above. Rabbit test serum was serially diluted 1/1000 with serum diluent (1.75% [w/v] nonfat dry milk, 0.005% thimerosal, 0.0025% Antifoam A, 0.5% normal goat serum in 20 mM sodium citrate). Two drops of diluted test serum was added to the membrane and incubated for 5 minutes. The membrane was washed, with 2 ml of 0.5% Tween 20/Tris-saline buffer. Two drops of goat anti-rabbit immunoglobulin/alkaline phosphatase conjugate diluted 1/500 with serum diluent were added and incubated for another 5 minutes. Two ml of 0.05% Tween/Tris-saline was then added to remove the excess enzyme conjugate. Two drops of the substrate solution was then added and incubated for another 2 minutes. Signal generated was detected visually or quantitated by reflectometry. As summarized in Table IV anti-human IgG in serum from hyperimmunized rabbit was easily detectable after dilution at 1/16,000.

TABLE IV

Detection of Rabbit Anti-Human IgG by a Second Antibody Sandwich Assay in a Filtration Format

| Sample | Dilution | Peak Weight |
|---|---|---|
| Normal Rabbit Serum | — * | 1.8 |
| Anti-Human IgG | 1/1,000 | 77.5 |
| Anti-Human IgG | 1/4,000 | 55.5 |
| Anti-Human IgG | 1/16,000 | 34.8 |

EXAMPLE VI

Competitive Assay for Detection of Antigen Using Multiple Membrane Layers

Goat anti-rabbit IgG was detected in this format by conjugating rabbit IgG to A-poly 32 by the procedure described in Example I.B. A test solution of anti-rabbit IgG was combined with 100 μl of rabbit IgG/A-poly 32 conjugate and 100 μl of goat anti-rabbit IgG/alkaline phosphatase in Tris/saline/1% BSA buffer and incubated for 10 minutes at 25° C. Anti-alkaline phosphatase was conjugated to A-poly 32 as described above and immobilized on 1.2 u pore size cellulose acetate membrane. The test solution was passed through two layers of 0.8 u pore size cellulose.acetate membrane attached to the bottom of a funnel which was in contact with the anti-enzyme activated cellulose acetate membrane. After the test solution had passed through the membrane layers the funnel and its attached membranes were removed and the anti-enzyme activated cellulose acetate membrane was washed once with 0.05% Tween-20/Tris-saline (2 ml) and two drops of the substrate solution was added and incubated for 3 minutes. A positive signal was observed visually or quantitated by reflectometry.

EXAMPLE VII

Antigen Capture Assay for Strep A

A. One Step Assay

The assay was performed by adding the following reagents: 150 ul of sample diluent containing polymer-Mab conjugate directed to Streptococcus A cell wall polysaccharide (18C9, Genetic Systems Corporation, Seattle, Wa., 2 ug/assay), polyclonal anti-Strep A-alkaline phosphatase conjugate made by substantially the procedure of Ishikawa, E. (*J. Immunoassay*, 1983, 4:275) and 50 ul of antigen extract. Extraction of the cell wall antigen was carried out by the nitrous acid extraction procedure described by Sleflein and Gil (*J. Clin. Microbiol.* 15:187, 1982). Incubation of the above mixture was for 20 minutes, and the mixture was then added to a well of a dot blot apparatus which contained a preblocked (1%, BSA/PBS, 1 hour) sheet of cellulose acetate membrane. The membrane was washed twice with 200 ul of 0.05% Tween 20 in Tris-buffered saline before transfer to a substrate-containing solution. After the desired reaction time, the membrane was removed from the substrate solution and washed with distilled water to stop the color reaction. The presence of Strep A antigen was determined by quantitation using reflectance spectroscopy (Table V). The presence of Strep A antigen can be determined visually by the appearance of the colored product developed by the reaction of alkaline phosphatase and the substrate.

TABLE V

Quantitation of Reflectance Obtained by Enzyme Membrane Affinity Concentration Immunoassay

| Number of Organisms/Assay | Experiment 1 (mV) | Experiment 2 (mV) |
|---|---|---|
| $1 \times 10^5$ | 8.567 | 7,546 |
| $5 \times 10^4$ | 4,666 | 5,090 |
| $1 \times 10^4$ | 909 | 827 |
| $5 \times 10^3$ | 535 | 465 |
| $1 \times 10^3$ | 31 | — |
| 0 | 0 | 0 |

B. Two Step Assay

Polyclonal anti-Step A capture antibody/polymer conjugate was prepared as described in Example I.B. and 0.14 ug was diluted in 1% BSA/Tris-saline. Eighty microliters were mixed with 150 ul of antigen extract prepared as above and the mixture was incubated for 1 minute at 25° C. The mixture was then added to a well of a dot blot apparatus which contained a preblocked (1% BSA/Tris-saline, pH 7.5, 1 hr) 1.2 u pore size cellulose acetate membrane. Polyclonal anti-Strep A antibody/alkaline phosphatase conjugate diluted in 1% BSA/Tris-saline (30 ul) was then added to the well and incubated for 2 minutes at 25° C. The membrane was washed twice with 200 u of 0.05% Tween 20 in Tris-saline before transfer to substrate (16.5 mg, 5-bromo-4-chloro-3-indoxyl phosphate; 8.5 mg, nitro blue tetrazolium per 50 ml Tris buffer, pH 0.6, containing 5 mM $MgCl_2$ and 0.1M NaCl). After two minutes of incubation, the membrane was removed from the substrate and washed with distilled water to stop the color reaction.

The presence of Strep A antigen was determined visually by the appearance of the colored product developed. The sensitivity of the assay was adjusted by altering the incubation time for color development. Longer incubation times resulted in a more intense color and greater sensitivity. This assay was adjusted so that $6 \times 10^3$ organisms per assay were detectable.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for determining the presence and/or concentration of an analyte in a biological fluid sample, comprising:

conjugating a first reactant, which specifically binds with said analyte, to a polymer comprising monomers of N-alkylacrylamides, N-arylacrylamides, alkyl acrylates or aryl acrylates, and combinations thereof to form a polymer/reactant conjugate;

conjugating a second reactant, which specifically binds with said analyte, to a reporter to form a reporter/reactant conjugate;

admixing in solution in the substantial absence of unconjugated polymer said polymer/reactant conjugate, reporter/reactant conjugate and said biological fluid sample suspected of containing said analyte to form a reaction mixture, such that specific binding occurs between said first and second reactants and said analyte, thereby forming a ternary complex;

contacting the reaction mixture with a solid phase comprising cellulose acetate or a cellulose ester which selectively binds by noncovalent means said polymer/reactant conjugate and said ternary complex, thereby removing said complex from the reaction mixture; and measuring the amount of reporter activity in the bound complex or in solution and therefrom determining the presence and/or concentration of said analyte.

2. The method of claim 1, including, after the step of contacting, washing the solid phase to remove nonspecifically bound reporter.

3. The method of claim 1 wherein the solid phase is a cellulose acetate membrane.

4. The method of claim 3 wherein said membrane has been treated to minimize nonspecific protein binding.

5. The method of claim 1, including, after the step of conjugating said first reactant to said polymer, purifying said polymer/reactant conjugate.

6. The method of claim 1, including, after the step of contacting, eluting from the solid phase the bound ternary complex or the reporter/reactant conjugate portion of the bound complex.

7. The method of claim 1, including, after the step of contacting, eluting from the solid phase the reporter portion of the bound ternary complex, wherein the reporter is conjugated to the reactant by a labile linkage.

8. The method of claim 1 wherein the step of contacting comprises filtering the reaction mixture through the solid phase.

9. The method of claim 1 wherein said analyte is selected from the group consisting of drugs, vitamins, hormones, DNA, proteins, metabolites, cells, haptens, viruses and microorganisms.

10. The method of claim 1 wherein said first and second reactants are selected from the group consisting of antibodies, antigens, lectins, receptors, transport proteins, peptides and non-immunoglobulin antibody-binding proteins.

11. The method of claim 1 wherein said reporter is selected from the group consisting of enzymes, fluorophores, radioisotopes, luminescers and dye particles.

12. The method of claim 1 wherein said reporter is an enzyme, and the step of measuring includes exposing the bound ternary complex to substrate and incubating for color or fluorescence development.

13. The method of claim 1 wherein said reporter is a fluorophore selected from the group consisting of fluorescein, rhodamine, phycoerythrin, phycocyanin and nile blue.

14. The method of claim 1 wherein said reporter is an enzyme selected from the group consisting of horseradish peroxidase, Beta-galactosidase, glucose oxidase, urease, Beta-lactamase and alkaline phosphatase.

15. The method of claim 1 wherein said first and second reactants are antibodies and said analyte is an antigen.

16. The method of claim 1 wherein said first and second reactants are antigens and said analyte is an antibody.

17. The method of claim 1 wherein said polymer is characterized by a lower critical solution temperature.

18. The method of claim 1 wherein said polymer is poly-N-isopropylacrylamide or derivatives thereof.

19. The method of claim 1 wherein said polymer is a copolymer formed from selected monomers.

20. The method of claim 19 wherein said copolymer is formed from N-isopropylacrylamide, N-n-butylacrylamide and N-acryloxysuccinimide monomers.

21. The method of claim 19 wherein said copolymer is formed from N-isopropylacrylamide monomers and N-acryloxysuccinimide monomers copolymerized with monomers selected from the group consisting of n-amyl acrylate, iso-amyl acrylate, n-octyl acrylate, methyl acrylate, ethyl acrylate, hexadecyl acrylate, 3,5,5-trimethylhexyl acrylate, N-tert-butylacrylamide, N-decylacrylamide, N-tert-octylacrylamide, N-benzylacrylamide, N-iso-butoxymethylacrylamide, and diacetone acrylamide.

22. A method for determining the presence and/or concentration of an analyte in a biological fluid sample, comprising:

conjugating a first reactant, which specifically binds with said analyte, to a monomer which comprises N-alkylacrylamides, N-arylacrylamides, alkyl acrylates or aryl acrylates, and combinations thereof to form a monomer/reactant conjugate;

copolymerizing said monomer/reactant conjugate with additional monomers to yield a copolymer/-reactant conjugate;

conjugating a second reactant, which specifically binds with said analyte, to a reporter to form a reporter/reactant conjugate;

admixing in solution in the substantial absence of unconjugated polymer said copolymer/reactant conjugate, reporter/reactant conjugate, and said biological fluid sample suspected of containing said analyte to form a reaction mixture, such that specific binding occurs between said first and second reactants and said analyte, thereby forming a ternary complex;

contacting the reaction mixture with a solid phase comprising cellulose acetate or cellulose esters which selectively binds by noncovalent means said polymer/reactant conjugate and said ternary complex, thereby removing said complex from the reaction mixture; and measuring the amount of reporter activity in the bound complex or in solution and therefrom determining the presence and/or concentration of said analyte.

23. A method for determining the presence and/or concentration of an analyte in a biological fluid sample, comprising:

in the substantial absence of unconjugated polymer, contacting a polymer/reactant conjugate, which specifically binds with said analyte and wherein said polymer is comprised of monomers selected from N-alkylacrylamides, N-arylacrylamides, alkyl acrylates and aryl acrylates, and combinations thereof, with a nonhydrophobic solid phase comprising cellulose acetate or a cellulose ester which binds by noncovalent means with said polymer/-reactant;

contacting the polymer/reactant-solid phase with a biological fluid sample suspected of containing said analyte such that specific binding occurs between said polymer/reactant and said analyte;

contacting said solid phase having the polymer/reactant/analyte complex bound thereto with a reporter/reactant conjugate which specifically binds with said analyte, such that specific binding occurs between said reporter/reactant and said analyte; and measuring the amount of reporter activity in the bound complex, and therefrom determining the presence and/or concentration of said analyte.

24. A method for determining the presence and/or concentration of an analyte in a biological fluid sample, comprising:

conjugating a first reactant to a polymer comprising monomers selected from N-alkylacrylamides, N-arylacrylamides, alkyl acrylates, aryl acrylates, and combinations thereof, to form a polymer/reactant conjugate;

conjugating a second reactant to a reporter to form a reporter/reactant conjugate, said second reactant which specifically binds with said analyte and said first reactant;

admixing in solution in the substantial absence of unconjugated polymer said polymer/reactant conjugate, reporter/reactant conjugate and said biological fluid sample suspected of containing said analyte to form a reaction mixture, such that competitive binding occurs between said polymer/-reactant conjugate and said analyte for said second reactant;

contacting said reaction mixture with a solid phase comprising cellulose acetate or an ester of cellulose, which selectively binds by noncovalent means the polymer/reactant conjugate and the polymer/-reactant-reporter/reactant complex, thereby removing said complex and said polymer/reactant from the reaction mixture; and measuring the amount of reporter activity in the bound complex or in the solution and therefrom determining the presence and/or concentration of the analyte.

25. A method for conducting multiple analyses on a single biological fluid sample suspected of containing one or more analytes, comprising:

conjugating a plurality of selected first reactants which specifically bind with a different analyte to a polymer comprising monomers selected from N-alkylacrylamides, N-arylacrylamides, alkyl acrylates, aryl acrylates or combinations thereof;

conjugating a plurality of selected second reactants which specifically bind with a different analyte to one or more selected reporters to form multiple reporter/reactant conjugates;

admixing in solution in the substantial absence of unconjugated polymer the multiple polymer/reactant, multiple reporter/reactant, and the biological fluid sample suspected of containing one or more analytes, such that specific binding occurs between the reactants and the analytes, thereby forming a plurality of ternary complexes;

contacting the admixed polymer/reactant conjugate, reporter/reactant conjugate, and analyte containing solution with a solid phase comprising cellulose acetate or a cellulose ester which selectively binds by noncovalent means the multiple polymer/reactant conjugates and the ternary complexes, thereby removing the complexes from the reaction mixture; and measuring the activity of each selected reporter associated with the bound complexes or in the solution and therefrom determining the presence and/or concentration of each of the analytes.

26. The method of claim 25 wherein the reporters are selected from the group consisting of enzymes, fluorophores, radioisotopes, luminescers and dye particles.

27. The method of claim 25 wherein the reporter is a fluorophore selected from the group consisting of fluorescein, rhodamine, phycoerythrin, phycocyanin and nile blue.

28. The method of claim 25 wherein the reporter is an enzyme selected from the group consisting of horseradish peroxidase, Beta-galactosidase, glucose oxidase, urease, Beta-lactamase and alkaline phosphatase.

29. The method of claim 25 wherein the solid phase is a cellulose acetate membrane.

30. A method for conducting multiple analyses on a biological fluid sample suspected of containing one or more analytes, comprising:

conjugating a plurality of selected first reactants which bind to different analytes to a plurality of polymers comprising monomers selected N-alkylacrylamides, N-arylacrylamides, alkyl acrylates, aryl acrylates or combinations thereof, having varied specific affinities for a non-hydrophobic solid phase comprising cellulose acetate or esters of cellulose to form multiple polymer/reactant conjugates, each of said first reactants which specifically binds with one of the analytes;

conjugating a plurality of selected second reactants which specifically bind with different analytes to one or more reporters to form multiple reporter/-reactant conjugates;

admixing in solution in the substantial absence of unconjugated polymer the multiple polymer/reactant conjugate, multiple reporter/reactant conjugates, and the biological fluid sample suspected of containing one or more analytes, such that specific binding occurs between the reactants and the analytes, thereby forming a plurality of ternary complexes;

contacting the admixed polymer/reactant conjugate, reporter/reactant conjugates, and analyte sample-containing solution with the solid phase which selectively binds by noncovalent means the unbound multiple polymer/reactants and the ternary complexes, thereby removing the complexes from the reaction mixture;

selectively eluting said ternary complexes from the solid phase; and measuring the reporter activity associated with each of the eluted complexes, and therefrom determining the presence and/or concentration of each of the analytes.

31. The method of claim 30 wherein said reporter is selected from the group consisting of enzymes, fluorophores, radioisotopes, luminescers and dye particles.

32. The method of claim 30 wherein the solid phase is a cellulose acetate membrane.

33. The method of claim 30 wherein the ternary complexes are selectively eluted using an ionic detergent, a non-ionic detergent, or a chaotropic agent.

34. A method for determining the presence and/or concentration of an analyte in a biological fluid sample, comprising:

conjugating a first reactant which specifically binds the analyte to a polymer comprising monomers selected from N-alkylacrylamides, N-arylacrylamides, alkyl acrylates, aryl acrylates or combinations thereof, to form a polymer/reactant conjugate;

conjugating a second reactant to a reporter to form a reporter/reactant conjugate, said second reactant being a competitor for specific binding to the first reactant with the analyte;

admixing in solution in the substantial absence of unconjugated polymer said polymer/reactant conjugate, reporter/reactant conjugate and said biological fluid sample suspected of containing said analyte to form a reaction mixture, such that competitive binding occurs between said reporter/-reactant conjugate and said analyte for said first reactant;

contacting said reaction mixture with a solid phase comprising cellulose acetate or an ester of cellulose which selectively binds by noncovalent means the polymer/reactant-reporter/reactant complexes and the polymer/reactant conjugate from the reaction mixture to form a resultant solution;

immobilizing a third reactant to a second solid phase to form a reactant-activated solid phase, said third reactant which specifically binds the reporter in the reporter/reactant conjugate;

contacting the resultant solution with the reactant-activated solid phase, thereby removing the reporter/reactant conjugate from the resultant solution; and measuring the reporter activity in the bound reporter/reactant conjugate and therefrom determining the presence and/or concentration of the analyte.

* * * * *